(12) United States Patent
Dewey et al.

(10) Patent No.: US 11,890,205 B2
(45) Date of Patent: Feb. 6, 2024

(54) SPINAL IMPLANT SYSTEM AND METHODS OF USE

(71) Applicant: Warsaw Orthopedic, Inc., Warsaw, IN (US)

(72) Inventors: Jonathan M. Dewey, Memphis, TN (US); Daniel A. Shimko, Memphis, TN (US); Mark C Dace, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 78 days.

(21) Appl. No.: 16/713,952

(22) Filed: Dec. 13, 2019

(65) Prior Publication Data

US 2021/0177622 A1    Jun. 17, 2021

(51) Int. Cl.
| | |
|---|---|
| *A61F 2/46* | (2006.01) |
| *A61F 2/44* | (2006.01) |
| *A61B 34/20* | (2016.01) |
| *A61B 90/00* | (2016.01) |
| *A61F 2/30* | (2006.01) |
| *A61B 17/56* | (2006.01) |

(52) U.S. Cl.
CPC ............ *A61F 2/4611* (2013.01); *A61B 34/20* (2016.02); *A61F 2/4465* (2013.01); *A61F 2/4684* (2013.01); *A61B 2017/564* (2013.01); *A61B 2034/2051* (2016.02); *A61B 2034/2063* (2016.02); *A61B 2034/2072* (2016.02); *A61B 2090/3764* (2016.02); *A61B 2090/3945* (2016.02); *A61F 2002/3008* (2013.01); *A61F 2002/4663* (2013.01); *A61F 2310/00023* (2013.01); *A61F 2310/00179* (2013.01); *A61F 2310/00359* (2013.01)

(58) Field of Classification Search
CPC ........ A61F 2/46; A61F 2/4611; A61F 2/4657; A61F 2002/4663–4664; A61B 2034/2046; A61B 2034/2051; A61B 2034/2074; A61B 5/05; A61B 34/20
See application file for complete search history.

(56) References Cited

U.S. PATENT DOCUMENTS

| | | |
|---|---|---|
| 5,592,939 A | 1/1997 | Martinelli |
| 5,913,820 A | 6/1999 | Bladen et al. |
| 6,021,343 A | 2/2000 | Foley et al. |
| 6,725,080 B2 | 4/2004 | Melkent et al. |
| 6,796,988 B2 | 9/2004 | Melkent et al. |
| 6,940,941 B2 | 9/2005 | Gregerson et al. |

(Continued)

*Primary Examiner* — Eduardo C Robert
*Assistant Examiner* — Michelle C Eckman
(74) *Attorney, Agent, or Firm* — Harness, Dickey & Pierce, P.L.C.

(57) ABSTRACT

A method for treating a spine comprises the steps of: inserting a surgical instrument into a tissue cavity, the surgical instrument including an image guide oriented relative to a sensor to communicate a signal representative of a position of the surgical instrument relative to the tissue cavity; displaying a selected configuration with a distal end of the surgical instrument in the tissue cavity; tracking movement of the selected configuration in the tissue cavity with a tracking device that communicates with a processor to generate data for display of the movement; and determining a volume of the tissue cavity based on the data. Systems, spinal constructs, implants and surgical instruments are disclosed.

20 Claims, 14 Drawing Sheets

(56) References Cited

U.S. PATENT DOCUMENTS

| | | | |
|---|---|---|---|
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 8,057,407 B2 | 11/2011 | Martinelli et al. | |
| 8,571,638 B2 | 10/2013 | Shoham | |
| 8,842,893 B2 | 9/2014 | Teichman et al. | |
| 2005/0038514 A1* | 2/2005 | Helm | A61F 2/4611 606/92 |
| 2005/0049486 A1* | 3/2005 | Urquhart | A61B 34/20 600/429 |
| 2005/0245817 A1* | 11/2005 | Clayton | A61B 5/06 600/424 |
| 2007/0167741 A1* | 7/2007 | Sherman | A61B 34/20 600/424 |
| 2008/0065082 A1* | 3/2008 | Chang | A61B 17/1659 606/85 |
| 2008/0077241 A1* | 3/2008 | Nguyen | A61F 2/4684 606/85 |
| 2017/0325897 A1* | 11/2017 | Isaacs | A61B 6/5235 |
| 2018/0116824 A1* | 5/2018 | Dewey | A61F 2/442 |
| 2019/0365476 A1* | 12/2019 | Melkent | A61B 34/10 |

\* cited by examiner

SPINAL IMPLANT SYSTEM AND METHODS OF USE

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, kyphosis, scoliosis and other curvature abnormalities, tumor and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants such as bone fasteners and vertebral rods to provide stability to a treated region. These implants can redirect stresses away from a damaged or defective region while healing takes place to restore proper alignment and generally support the vertebral members. During surgical treatment, surgical instruments are employed, for example, to facilitate surgical preparation, manipulation of tissue and delivering implants to a surgical site. This disclosure describes an improvement over these prior technologies.

SUMMARY

In one embodiment, a method for treating a spine is provided. The method comprises the steps of: inserting a surgical instrument into a tissue cavity, the surgical instrument including an image guide oriented relative to a sensor to communicate a signal representative of a position of the surgical instrument relative to the tissue cavity; displaying a selected configuration with a distal end of the surgical instrument in the tissue cavity; tracking movement of the selected configuration in the tissue cavity with a tracking device that communicates with a processor to generate data for display of the movement; and determining a volume of the tissue cavity based on the data. In some embodiments, systems, spinal constructs, implants and surgical instruments are disclosed.

In one embodiment, the method comprises the steps of: inserting a distal end of a surgical instrument into an intervertebral cavity, the surgical instrument including a surgical navigation emitter oriented relative to a sensor to communicate a signal representative of a position of the surgical instrument relative to the intervertebral cavity; displaying a sphere with the distal end in the intervertebral cavity from a computer monitor; tracking movement of the surgical instrument in the intervertebral cavity with a tracking device and communicating with a processor to generate data for display of the movement from the computer monitor including generating a plurality of images of the sphere in the intervertebral cavity at discrete time intervals based on movement of the surgical instrument; and determining a volume of the intervertebral cavity based on the data.

In one embodiment, the method comprises the steps of: disposing a surgical instrument adjacent to a tissue cavity, the surgical instrument including an image guide oriented relative to a sensor to communicate a signal representative of a position of a distal end of the surgical instrument relative to the tissue cavity; displaying at least one trial with the distal end in the tissue cavity; tracking the surgical instrument relative to the tissue cavity with a tracking device that communicates with a processor to generate data for display of the at least one trial relative to the tissue cavity; and comparing the at least one trial relative to the tissue cavity to determine a volume of the tissue cavity.

BRIEF DESCRIPTION OF THE DRAWINGS

The present disclosure will become more readily apparent from the specific description accompanied by the following drawings, in which.

DETAILED DESCRIPTION

Figure 1:
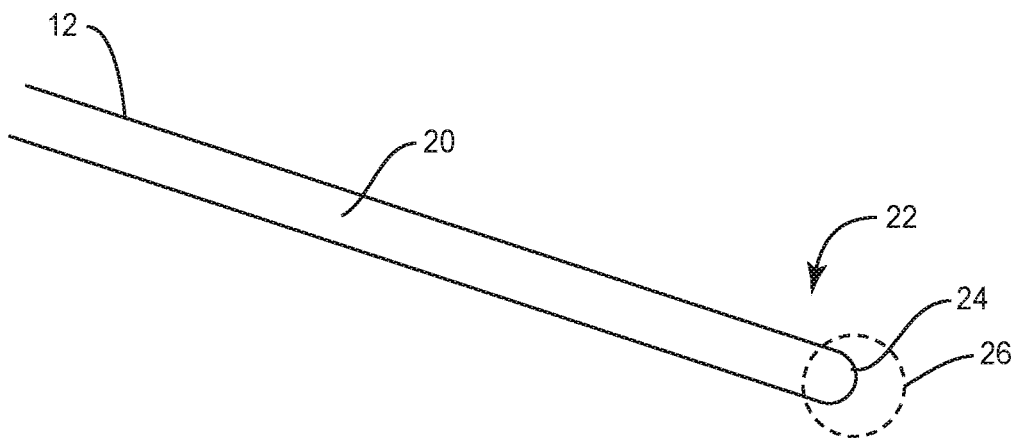
FIG. 1 is a side view of components including a graphical representation of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the systems and methods of the present disclosure comprise surgical navigation and medical devices including surgical instruments and implants that are employed with a surgical treatment, as described herein, for example, with a cervical, thoracic, lumbar and/or sacral region of a spine.

In some embodiments, the present surgical system and methods include graphical representation and images of patient anatomy, patient anatomy cavities and volumes, implants including bone graft and/or trials for surgical planning and performing surgical procedures. In some embodiments, the present surgical system is employed with methods that allow a surgeon to determine a size and/or configuration of patient anatomy, patient anatomy cavities and volumes, implants including bone graft and/or trials by projecting an image of patient anatomy, patient anatomy cavities and volumes, implants including bone graft and/or trials in a vertebral space from a computer display employing surgical navigation.

In some embodiments, the present surgical system includes a surgical navigation system and one or more processors for generating graphical representation and images of patient anatomy, patient anatomy cavities and volumes, implants, implants including bone graft and/or trials for surgical planning and performing surgical procedures, and is employed with a method of assessing a graft volume utilizing navigated images, as described herein. In some embodiments, one or more processors of the present surgical system execute one or more instructions and/or programming in operation of the surgical navigation system for generating navigated images, for example, navigated projections from surgical instruments. In some embodiments, the surgical system includes a surgical instrument, for example, a funnel having a navigation component. In some embodiments, the present surgical system is employed with a method for calculating an approximate graft volume of one or more patient anatomical cavities. In some embodiments, the present surgical system is employed with a method for determining an amount of intervertebral disc and/or vertebrae preparation. In some embodiments, the present surgical system is employed with a method for determining the amount of intervertebral disc area and/or vertebrae that needs to be removed in connection with surgical planning and performing surgical procedures. In some embodiments, the present surgical system is employed with a method for determining an amount of graft needed to be harvested from a patient and/or from non-patient sources and/or synthetics. In some embodiments, the present surgical system is employed with a method for labeling the navigated projections to indicate graft volume of one or more patient anatomical cavities.

In some embodiments, the present surgical system includes a surgical instrument having an image guide oriented relative to a sensor to communicate a signal representative of a position of a surgical instrument relative to a tissue cavity for generating an image of a distal end of the surgical instrument. In some embodiments, the surgical instrument includes a shaft having a linear distal end. In some embodiments, the surgical instrument includes a shaft having an angled distal end.

In some embodiments, the present surgical system includes a surgical instrument having a distal end, and one or more processors that execute one or more instructions and/or programming in operation of a surgical navigation system for generating navigated images, for example, a selected configuration, for example, a spherical configuration from the distal end in a tissue cavity. In some embodiments, the surgical navigation system executes one or more instructions and/or programming to initiate volume measurement of a tissue cavity. In some embodiments, the surgical instrument is moved within the tissue cavity and tracked by the surgical navigation system. In some embodiments, movement of the surgical instrument is tracked such that images and/or snap shots of the selected configuration are generated, for example, at discrete intervals such that the surgical navigation system tracks the surgical instrument and generates images of distal end movement. In some embodiments, the surgical instrument is moved along a path within the tissue cavity such that a distal end of the surgical instrument is moved and an image of the distal end of the surgical instrument moving in the tissue cavity is generated in a first dimension, a second dimension and/or a third dimension. In some embodiments, the surgical navigation system executes one or more instructions and/or programming to selectively stop volume measurement upon compilation of the images of the path of the distal end of the surgical instrument. In some embodiments, the surgical navigation system executes one or more instructions and/or programming to calculate a volume of each image, and/or the total volume of the image generated path of the distal end of the surgical instrument. In some embodiments, the captured images of the path of the distal end of the surgical instrument may overlap. In some embodiments, the surgical navigation system executes one or more instructions and/or programming to identify and/or determine the overlap. In some embodiments, the surgical navigation system executes one or more instructions and/or programming to subtract the overlap and calculate a volume of the path of the distal end of the surgical instrument.

In some embodiments, the present surgical system includes a surgical navigation system employed with methods for imaging a vertebral space, an intervertebral disc and/or vertebrae axially and/or laterally to determine a volume of a tissue cavity. In some embodiments, the present surgical system is employed with a method for determining a cross section and/or height of the tissue cavity to calculate a volume of the tissue cavity for disposal of an implant, which may include bone graft. In some embodiments, a surgical trial instrument is disposed adjacent the tissue cavity. In some embodiments, the present surgical system includes one or more processors that execute one or more instructions and/or programming in operation of a surgical navigation system for generating navigated images, for example, a trial projection with the surgical trial instrument, which includes an image guide oriented relative to a sensor to communicate a signal representative of a position of a surgical trial instrument relative to the tissue cavity for generating an image of a distal end of the surgical trial instrument. In some embodiments, an image of the surgical trial instrument is displayed relative to imaging of the tissue.

In some embodiments, the present surgical system includes a surgical navigation system and one or more processors that execute one or more instructions and/or programming for generating images of a selected configuration, for example, a kidney bean shaped trial projection from an end of the trial instrument. In some embodiments, the trial projection includes a selected volume. In some embodiments, the trial projection is selected from a plurality of alternately sized projections. In some embodiments, one or more trial projections are selected from a volume in a range of about 2.0 cc to about 12.0 cc. In some embodiments, one or more trial projections are selected from a volume in a range of about 2.9 cc to about 10.2 cc. In some embodiments, the one or more processors activate display or graphical representation of the trial projection.

In some embodiments, the present surgical system includes a surgical navigation system employed with methods for imaging a surgical trial instrument having a trial projection and a tissue cavity, as described herein, including the step of projecting a trial projection having a first volume, which may be a smaller volume, and comparing the trial projection having the first volume relative to the tissue cavity. In some embodiments, the method includes the step of manipulating the surgical trial instrument for alignment of the trial projection with the tissue cavity to assess if the volume of the trial projection substantially occupies the tissue cavity. In some embodiments, the method includes the step of determining if the trial projection having the first volume sufficiently occupies the tissue cavity and/or if a trial projection having a greater volume is needed. In some embodiments, the method includes the step of manipulating the surgical trial instrument for alignment of a trial projection having a second, larger volume with the tissue cavity to assess if the second volume substantially occupies the tissue cavity. In some embodiments, the method includes the step of determining if the trial projection having the second volume sufficiently occupies the tissue cavity and/or if a trial projection having a greater volume is needed. In some embodiments, the method includes the step of manipulating the surgical trial instrument for alignment of a trial projection having a third, larger volume with the tissue cavity to assess if the third volume substantially occupies the tissue cavity. In some embodiments, the method includes the step of assessing one or a plurality of alternate trial projections having a selected volume for disposal with a tissue cavity. In some embodiments, the method includes the step of determining if the trial projection having a selected volume sufficiently occupies the tissue cavity and/or if the trial projection is too small, too large, and/or may require removal of too much tissue that may compromise the annulus and/or injure the patient. In some embodiments, the features of the present surgical system and methods resist and/or prevent damage or injury to vertebral tissue. In some embodiments, the trial projection is adjustable, for example, to manipulate a height of the trial projection, which may, for example, facilitate determination of a volume of bone graft needed to fill a tissue cavity.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
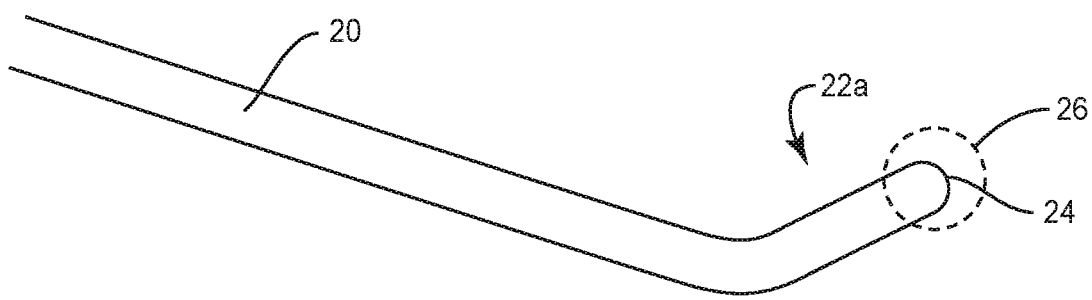
FIG. 2 is a side view of components including a graphical representation of one embodiment of a surgical system in accordance with the principles of the present disclosure.
Figure 3:
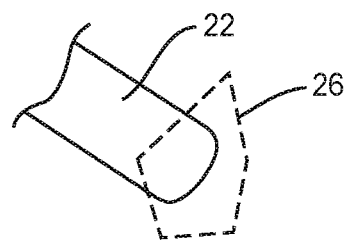
FIG. 3 is a break away view of components including a graphical representation of one embodiment of a surgical system in accordance with the principles of the present disclosure.

The following discussion includes a description of a surgical system including surgical navigation, surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, one or more of the components of surgical system 10 are configured for engagement with one or more components of one or more spinal constructs, which may include spinal implants, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine. In some embodiments, the spinal constructs can be attached with vertebrae in a revision surgery to manipulate tissue and/or correct a spinal disorder, as described herein.

Surgical system 10 includes a surgical instrument 12, which is employed with a surgical navigation system 14 and utilized for an intra-operative assessment of a volume of a tissue cavity C, for example, an intervertebral disc space, for determining an implant size and configuration and/or an amount of bone growth promoting material, for example, bone graft for disposal with tissue cavity C in connection with surgical planning and performing surgical procedures, as described herein. In some embodiments, the bone graft may include an agent, which may be disposed, packed, coated or layered within tissue cavity C. In some embodiments, the agent may be HA coating. In some embodiments, the agent may include one or a plurality of therapeutic agents and/or pharmacological agents for release, including sustained release, to treat, for example, pain, inflammation and degeneration.

Surgical instrument 12 includes a shaft 20. In some embodiments, shaft 20 is cannulated. In some embodiments, shaft 20 is configured to inject bone graft, for example, a funnel configuration. In some embodiments, shaft 20 includes a distal end 22. In some embodiments, distal end 22 includes a linear configuration, as shown in FIG. 1. In some embodiments, shaft 20 includes a distal end 22a having an angled configuration, as shown in FIG. 2. Distal end 22 includes a distal tip 24. Distal end 22 is configured for movement within tissue cavity C, as described herein.

Figure 4:
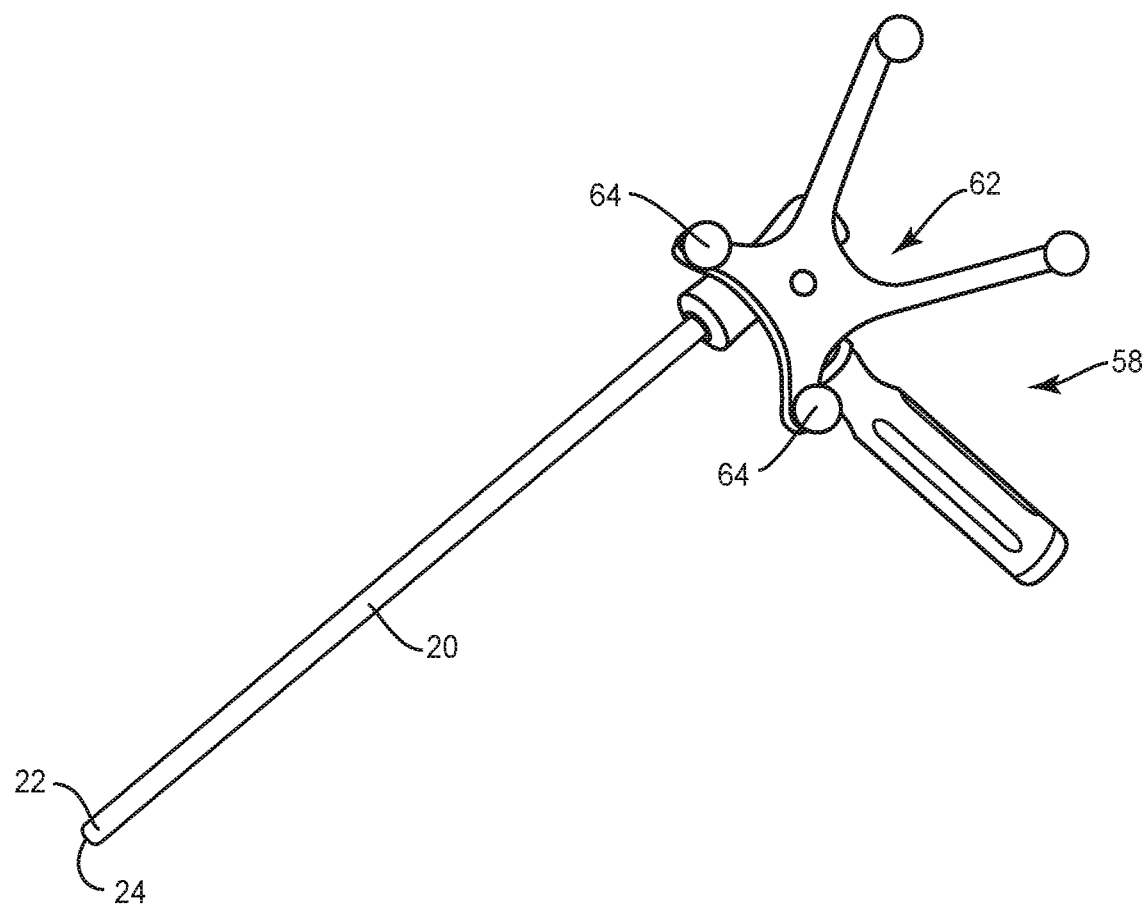
FIG. 4 is a perspective view of components of one embodiment of a surgical system in accordance with the principles of the present disclosure.

Surgical instrument 12 includes an image guide, for example, a navigation component 58, as shown in FIG. 4, which communicates with surgical navigation system 14 to monitor components of surgical system 10 and patient anatomy under surgical navigation. In some embodiments, navigation component 58 is connected with surgical instrument 12 via an integral connection, friction fit, pressure fit, interlocking engagement, mating engagement, dovetail connection, clips, barbs, tongue in groove, threaded, magnetic, key/keyslot and/or drill chuck.

Shaft 20 is positioned a selected distance from vertebral tissue in connection with surgical navigation and for generating an image of distal end 22 and tip 24 for display from a computer monitor, as described herein. Distal end 22 extends a distance measured from a proximal most end surface of shaft 20 in connection with image guidance. In some embodiments, this configuration provides indicia of the size, type and/or position of distal end 22 relative to shaft 20 and/or vertebral tissue. The components of surgical system 10 and surgical navigation system 14 allow a surgeon to determine a size and/or configuration of tissue cavity C for disposal of a selected volume of bone graft, by projecting an image of a selected configuration from tip 24 from a computer display.

Figure 5:
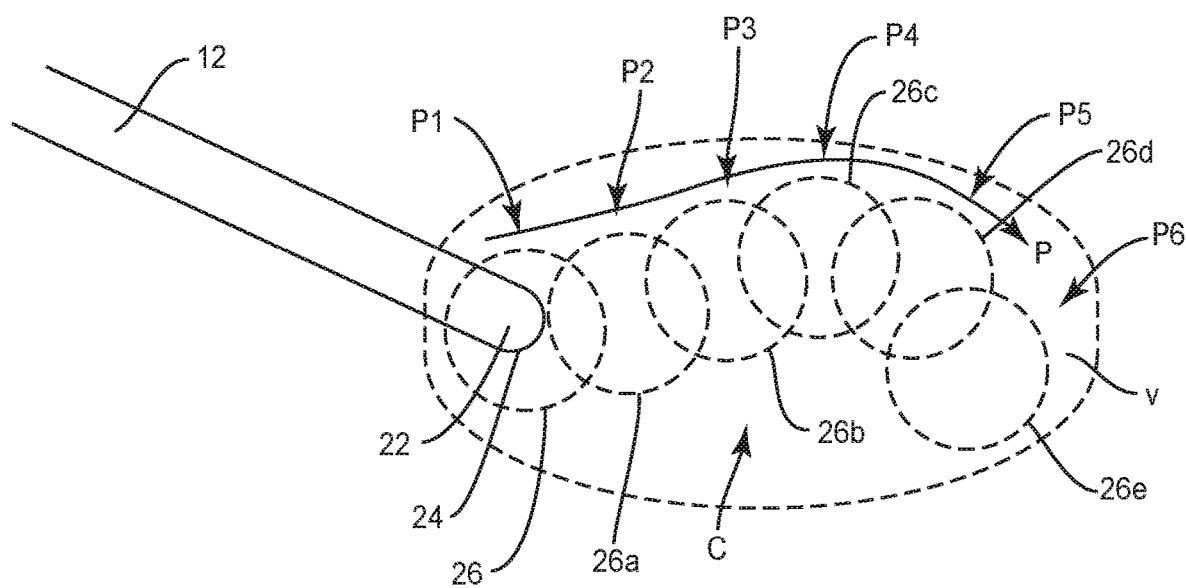
FIG. 5 is a graphical representation of a computer display of components of one embodiment of a surgical system in accordance with the principles of the present disclosure disposed with patient anatomy.

Surgical navigation system 14 is configured to project an image of a selected configuration, for example, a spherical projection 26 from tip 24, as shown in FIGS. 1, 2 and 5. Projection 26 is displayed from tip 24 having a selected volume V1 and/or the selected configuration of projection 26 includes selected measurements or indicia in two or three dimensions, for example, length, width, and height to calculate the volume of tissue cavity C for determining an implant size and configuration and/or an amount of bone growth promoting material in connection with surgical planning and performing surgical procedures. In some embodiments, the selected configuration may be polygonal, as shown in FIG. 3. In some embodiments, the selected configuration may have alternate configurations, for example, cubed, rectangular cross section, triangular cross section, oblong, barrel shaped, dog bone shaped, t shaped, undulating, staggered and/or offset. In some embodiments, the selected configuration includes a volume selected from a range of greater than zero through 5.0 cc. In some embodiments, the selected configuration includes a volume of 1.0 cc. In some embodiments, spherical projection 26 includes a diameter selected from a range of greater than zero through 20 mm.

Figure 6:
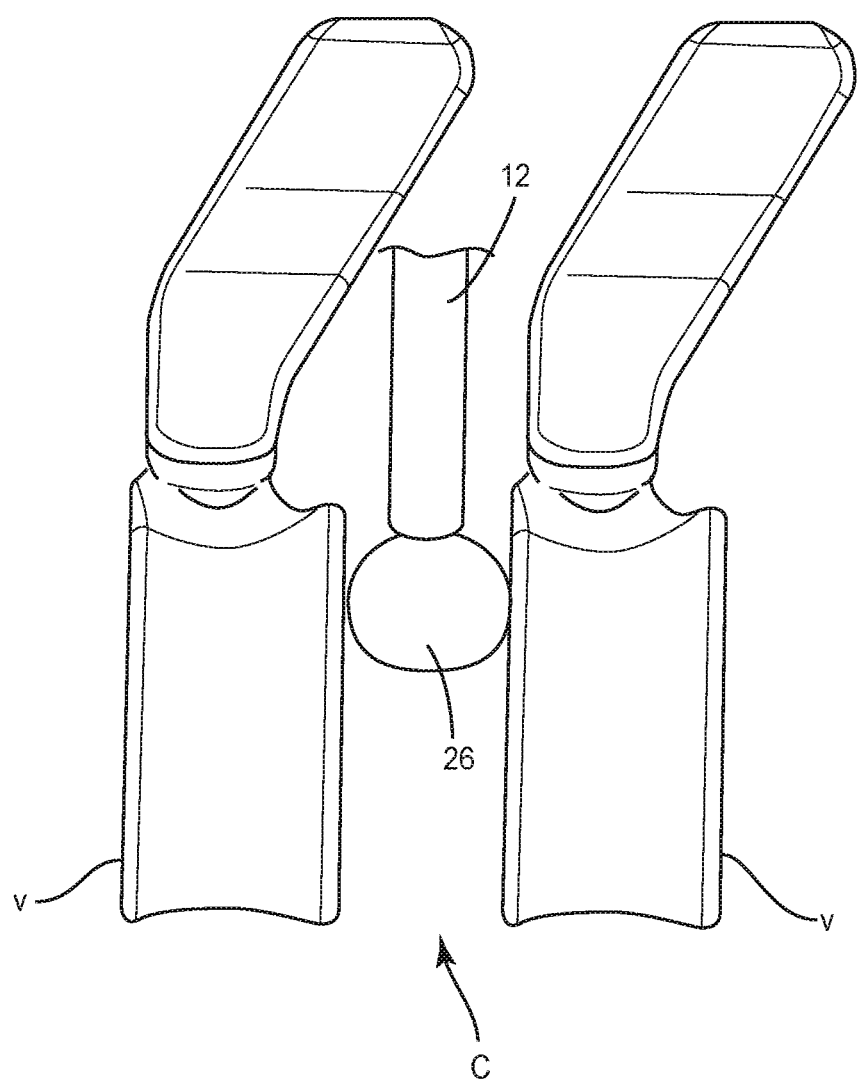
FIG. 6 is a graphical representation of a computer display of components of one embodiment of a surgical system in accordance with the principles of the present disclosure disposed with patient anatomy.

A graphical image of distal end 22 is displayed from a computer monitor and moved with projection 26 extending therefrom within tissue cavity C in a plane of tissue cavity C. In some embodiments, projection 26 is moved in the plane of tissue cavity C to identify and/or measure tissue cavity C in two or three dimensions, for example, length, width, and height to calculate the volume of tissue cavity C in connection with surgical planning and performing surgical procedures. For example, distal end 22 is moved along a path P, as shown in FIG. 5. As distal end 22 is moved within tissue cavity C, projection 26 is displayed from tip 24 to identify and/or measure tissue cavity C in two or three dimensions, for example, length, width, and height of an intervertebral space to calculate the volume of tissue cavity C, as shown in FIG. 6.

In some embodiments, a graphical image of tip 24 is displayed from a computer monitor and travels in the intervertebral disc space along the anatomical surfaces of vertebral tissue with projection 26 extending therefrom to identify and/or measure a selected area of tissue cavity C, for example, from an axial view of vertebrae, and/or a selected height of tissue cavity C, for example, from a lateral view of vertebrae. In some embodiments, navigation system 14 tracks the movement of surgical instrument 12 with sensors, as described herein, and graphically displays projection 26 from tip 24 along path P in two or three dimensions, for example, length, width, and height of the intervertebral space to calculate the volume of tissue cavity C. In some embodiments, navigation system 14 tracks the movement of surgical instrument 12 with sensors and determines/calculates movement of projection 26 extending from tip 24, graphically represented from a computer display, with one or more processors of navigation system 14, which execute one or more instructions and/or programming in operation of navigation system 14, in two or three dimensions, for example, length, width, and height of the intervertebral space to calculate the volume of tissue cavity C, as shown in FIG. 5.

Figure 7:
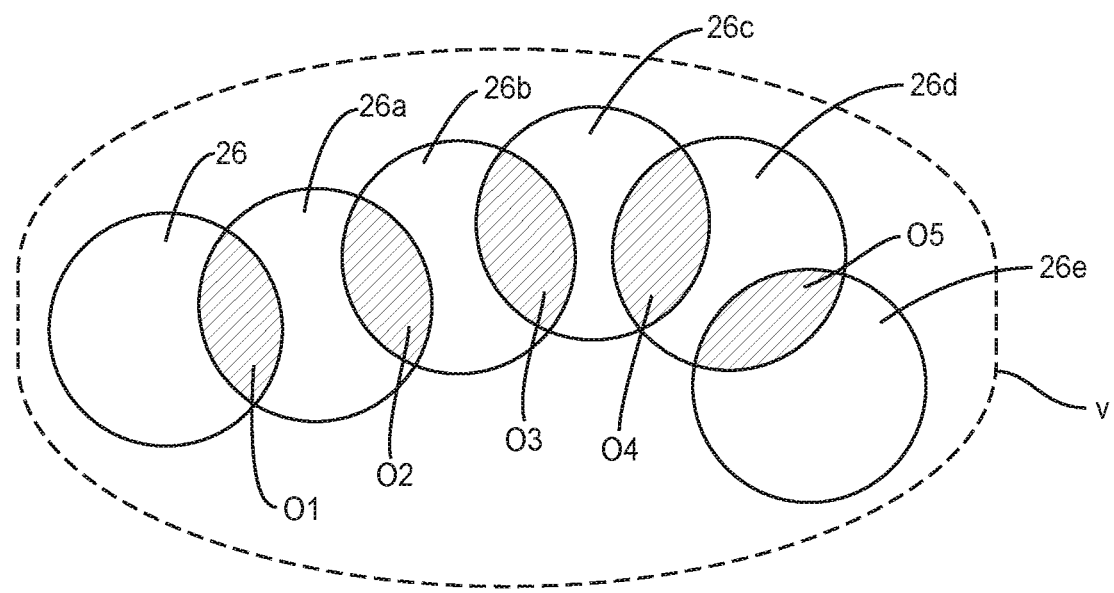
FIG. 7 is a graphical representation of a computer display of components of one embodiment of a surgical system in accordance with the principles of the present disclosure disposed with patient anatomy.
Figure 8:
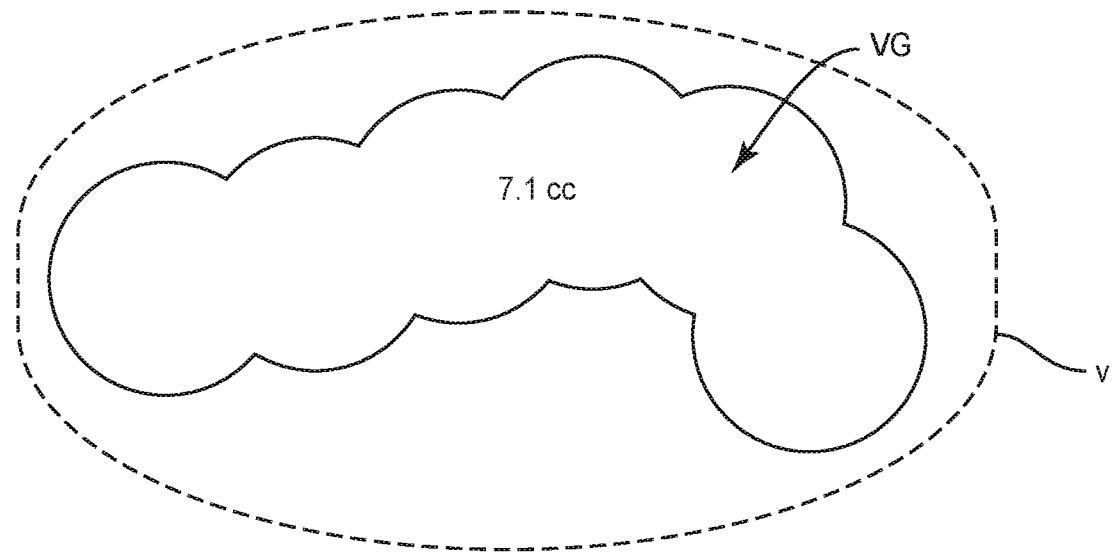
FIG. 8 is a graphical representation of a computer display of components of one embodiment of a surgical system in accordance with the principles of the present disclosure disposed with patient anatomy.

Navigation system 14 tracks movement of surgical instrument 12 along path P with projection 26 extending from tip 24 graphically displayed from a computer monitor 66. Computer monitor 66 displays travel of projection 26 along path P as a continuous path that is selectively moved in an intervertebral disc space to indicate, highlight and/or measure a selected area of the disc space, for example, from an axial view of vertebrae, and/or a selected height, for example, from a lateral view of vertebrae to calculate the volume of tissue cavity C, as shown in FIGS. 7 and 8.

Navigation component 58 includes an emitter array 62, as shown in FIG. 4. Emitter array 62 is configured for generating a signal to sensor array 60 of surgical navigation system 14. The signal generated by emitter array 62 includes data points that represent a position and/or orientation of one or more components of surgical system 10, for example, surgical instrument 12 traveling in tissue cavity C along the anatomical surfaces of vertebral tissue with projection 26 extending therefrom to identify and/or measure a selected area of tissue cavity C. In some embodiments, the signal generated by emitter array 62 includes data points that represent a three-dimensional position of surgical instrument 12 relative to tissue for generating an image of distal end 22 for display from monitor 66. In some embodiments, emitter array 62 may include a reflector array configured to reflect a signal from sensor array 60.

Emitter array 62 includes four spaced apart arms having a substantially X-shape. Emitter array 62 includes markers, for example, fiducials 64. Fiducials 64 appear in the image produced by surgical navigation system 14 for use as a point of reference or a measure. Emitter array 62 generates signals representing the position of various reference points of the patient's anatomy. See, for example, similar surgical navigation components and their use as described in U.S. Pat. Nos. 6,021,343, 6,725,080, and 6,796,988, the entire contents of each of these references being incorporated by reference herein. In some embodiments, fiducials 64 include at least one light emitting diode. In some embodiments, fiducials 64 may include other tracking devices capable of being tracked by sensor array 60, for example, a tracking device that actively generates acoustic signals, magnetic signals, electromagnetic signals, radiologic signals. In some embodiments, fiducials 64 may be removably attached to emitter array 62. In some embodiments, one or more of fiducials 64 each include a single ball-shaped marker.

Tracking system 72 can include various portions that are associated or included with surgical navigation system 14. In some embodiments, tracking system 72 can also include a plurality of types of tracking systems, such as, for example, an optical tracking system that includes an optical localizer, such as, for example, sensor array 60 and/or an EM tracking system that can include an EM localizer. Various tracking devices can be tracked with tracking system 72 and the information can be used by surgical navigation system 14 to allow for a display of a position of an item, for example, a patient tracking device, an imaging device tracking device 74, and an instrument tracking device, for example, emitter array 62, to allow selected portions to be tracked relative to one another with the appropriate tracking system. In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, and 5,592,939, the entire contents of each of these references being incorporated by reference herein.

Sensor array 60 is located in such a manner to provide a clear line of sight with emitter array 62, as described herein. In some embodiments, fiducial markers 64 of emitter array 62 communicate with sensor array 60 via infrared technology. Sensor array 60 is coupled to a computer 65, which may be programmed with software modules that analyze signals transmitted by sensor array 60 to determine the position of each object in a detector space.

One or more processors and/or software of surgical navigation system 14 execute one or more instructions and/or programming such that sensor array 60 tracks navigation component 58 attached with surgical instrument 12. Navigation component 58 includes emitter array 62 that generates a signal to sensor array 60, which includes data points that represent a position and/or orientation of surgical instrument 12 for generating data points, images and/or snap shots of tip 24 at one or a plurality of time intervals for generating projections 26 in connection with display of path P from computer monitor 66 to calculate the volume of tissue cavity C. In some embodiments, navigation component 58 communicates with sensor array 60 and surgical navigation system 14 to identify positional data points of tip 24 at one or a plurality of time intervals for generating projections 26 in connection with display of path P from computer monitor 66 to calculate the volume of tissue cavity C. See, for example, similar surgical navigation components, imaging and their use as described in U.S. Pat. Nos. 6,021,343, 6,725,080, 6,796,988, 6,940,941, 7,001,045, 7,106,825, 7,108,421, 7,188,998 and 8,842,893, the entire contents of each of these references being incorporated by reference herein.

Navigation component 58 generates a signal to sensor array 60. The signal includes data points representing a position and/or orientation of surgical instrument 12 for imaging position and/or orientation of tip 24 and projection 26 to facilitate capturing and generating imaging of path P for display from computer monitor 66. In some embodiments, movement of navigation component 58 attached with surgical instrument 12 is tracked by navigation system 14 to generate data points, images and/or snap shots of tip 24 and projection 26 at discrete time intervals. As tip 24 is moved along path P, movement of navigation component 58 attached with surgical instrument 12 is tracked by navigation system 14 using surgical navigation at discrete time intervals, for example, generating data points, images and/or snap shots of tip 24 and displaying projection 26 at positions P1, P2, P3, P4, P5 and P6, which are displayed from computer monitor 66 as a continuous path P, as shown in FIG. 8.

For example, movement of navigation component 58 attached with surgical instrument 12 is tracked by navigation system 14 using surgical navigation to generate data points, an image and/or a snap shot of tip 24 and projection 26 at a first time interval, which is displayed from computer monitor 66 at position P1, as shown in FIG. 5. At a second time interval, surgical instrument 12 is tracked by navigation system 14 to generate an image and/or a snap shot of tip 24 and projection 26a for display from computer monitor 66 at position P2. At a third time interval, surgical instrument 12 is tracked by navigation system 14 to generate data points, an image and/or a snap shot of tip 24 and projection 26b for display from computer monitor 66 at position P3. At a fourth time interval, surgical instrument 12 is tracked by navigation system 14 to generate data points, an image and/or a snap shot of tip 24 and projection 26c for display from computer monitor 66 at position P4. At a fifth time interval, surgical instrument 12 is tracked by navigation system 14 to generate data points, an image and/or a snap shot of tip 24 and projection 26d for display from computer monitor 66 at position P5. At a sixth time interval, surgical instrument 12 is tracked by navigation system 14 to generate data points, an image and/or a snap shot of tip 24 and projection 26e for display from computer monitor 66 at position P6. In some embodiments, surgical instrument 12 is tracked by navigation system 14 to generate data points, images and/or snap shots of tip 24 at one or a plurality of time intervals for projecting projection 26 in connection with display of path P from computer monitor 66 to calculate the volume of tissue cavity C, as described herein. In some embodiments, the time interval may be selected from a range of duration, for example, a time greater than zero seconds through 1.0 seconds. In some embodiments, the time interval includes 0.5 seconds. In some embodiments, the intervals between images and/or snap shots of tip 24 are not based on a time interval, but based on the relative movement of tip 24 from a prior position. In some instances the relative movement which triggers new images is between 0.25 mm and 5 mm. In some embodiments, the relative movement which triggers new images is 1 mm.

In some embodiments, one or more processors and/or software of surgical navigation system 14 execute one or more instructions and/or programming to selectively stop tracking of surgical instrument 12 corresponding to generating imaging and/or data points of tip 24 and projection 26, for example, upon indication, highlight and/or measurement of a selected area of the disc space, for example, from an axial view of vertebrae, and/or a selected height, for example, from a lateral view of vertebrae to calculate the volume of tissue cavity C.

In some embodiments, one or more processors and/or software of surgical navigation system 14 execute one or more instructions and/or programming to calculate a total volume V2 of path P corresponding to the selected area and/or height of the intervertebral disc space, and based on the selected volume of projection 26.

In some embodiments, an algorithm calculates a volume V2 of tissue cavity C from projections 26, 26a, 26b, 26c, 26d and 26e each having the selected volume V1, in connection with determining an implant size and configuration and/or an amount of bone growth promoting material in connection with surgical planning and performing surgical procedures.

1) Multiply the number of projections 26 by the selected volume V1:

$$6V1=V2$$

In some embodiments, the images of projections 26, 26a, 26b, 26c, 26d and 26e may overlap. In some embodiments, one or more processors and/or software of surgical navigation system 14 execute one or more instructions and/or programming to identify and/or determine the overlap of projections 26, for example, overlap O1, overlap O2, overlap O3, overlap O4 and overlap O5, as shown in FIG. 7. In some embodiments, one or more processors and/or software of surgical navigation system 14 execute one or more instructions and/or programming to subtract overlap O1, overlap O2, overlap O3, overlap O4 and overlap O5 from volume V2 to calculate an actual volume VG. In some embodiments, the present algorithm calculates volume VG of tissue cavity C, in connection with determining an implant size and configuration and/or an amount of bone growth promoting material in connection with surgical planning and performing surgical procedures, as shown in FIG. 8.

2) To determine a volume VG:

$$V2-(O1+O2+O3+O4+O5)=VG$$

In some embodiments, distal end 22 and/or tip 24 includes indicia, for example, radiopaque markers. In some embodiments, the markers facilitate viewing and/or identification of the size, configuration, orientation and/or positioning of surgical instrument 12 in space and/or relative to vertebral tissue under x-ray, fluoroscopy, CT or other imaging techniques by surgical navigation system 14, as described herein.

In some embodiments, surgical navigation system 14 includes an image capturing portion 70 that may include an x-ray source or emission portion and an x-ray receiving or image receiving portion located generally or as practically possible 180 degrees from each other and mounted on a rotor (not shown) relative to a track of image capturing portion 70. Image capturing portion 70 can be operable to rotate 360 degrees during image acquisition. Image capturing portion 70 may rotate around a central point or axis, allowing image data of the patient to be acquired from multiple directions or in multiple planes. Surgical navigation system 14 can include image capturing devices, for example, such as those disclosed in U.S. Pat. Nos. 8,842,893; 7,188,998; 7,108,421; 7,106,825; 7,001,045; and 6,940,941; the entire contents of each of these references being incorporated by reference herein. In some embodiments, surgical navigation system 14 can include medical imaging, for example, C-arm fluoroscopic imaging systems, which can generate three-dimensional views of a patient. The position of image capturing portion 70 can be precisely known relative to any other portion of an imaging device of navigation system 14. In some embodiments, a precise knowledge of the position of image capturing portion 70 can be used in conjunction with a tracking system 72 to determine the position of image capturing portion 70 and the image data relative to the patient. In some embodiments, one or more processors and/or software of surgical navigation system 14 execute one or more instructions and/or programming in operation of image capturing portion 70 for acquiring and/or capturing data points, images and/or snap shots of tip 24 at one or a plurality of time intervals for projecting projections 26 in connection with display of path P from computer monitor 66 to calculate the volume of tissue cavity C, similar to that described herein.

In assembly, operation and use, surgical system 10, similar to the systems and methods described herein, is employed with a surgical procedure, for treatment of a spine of a patient including vertebrae v and insertion of bone graft into a tissue cavity, for example, an intervertebral disc space C, as shown in FIGS. 5 and 6. Surgical system 10 may also be employed with surgical procedures, for example, discectomy, laminectomy, fusion, laminotomy, laminectomy, nerve root retraction, foramenotomy, facetectomy, decompression, spinal nucleus or disc replacement and implantable prosthetics including plates, rods, and bone engaging fasteners.

Figure 9:
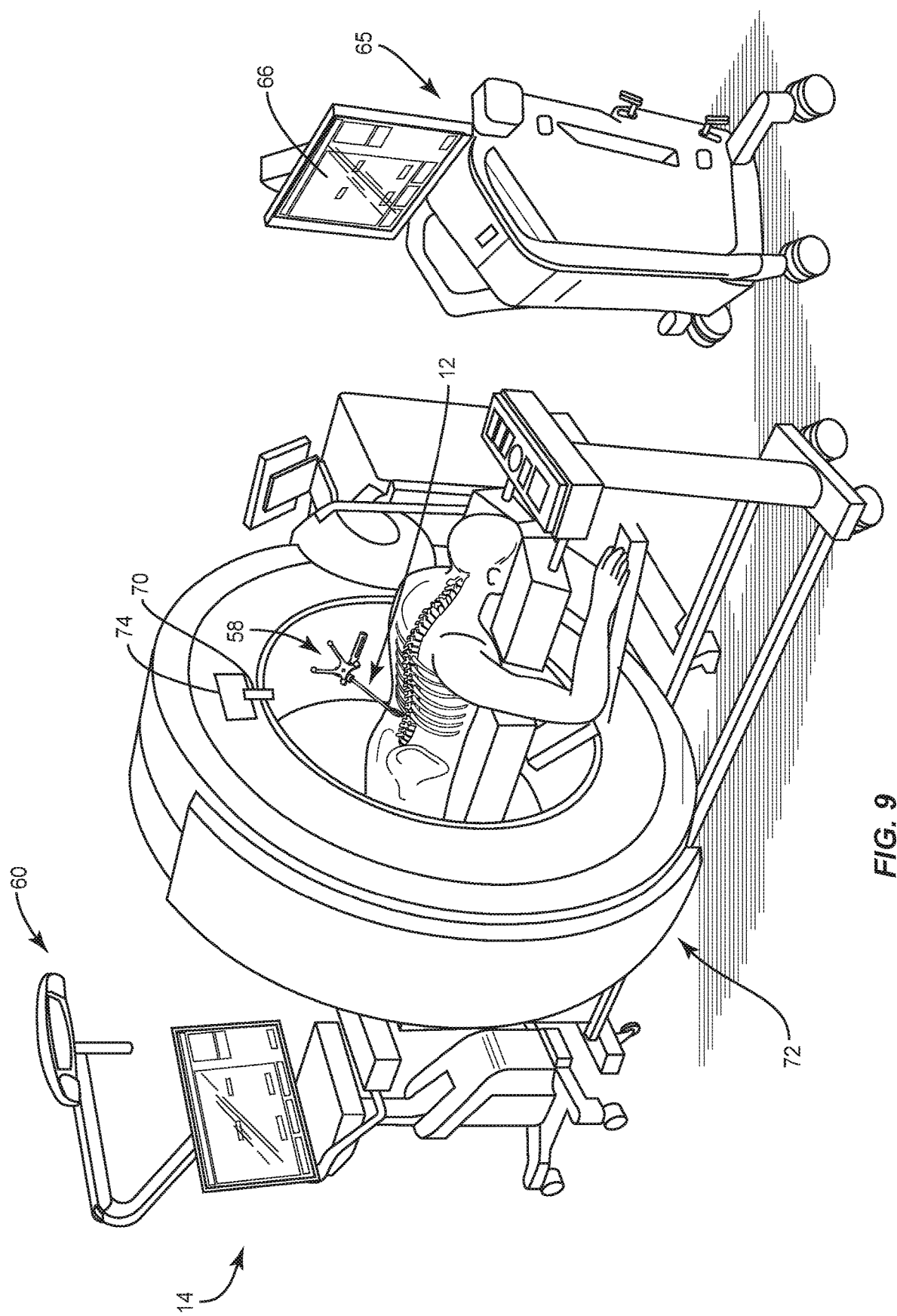
FIG. 9 is a perspective view of components of one embodiment of a surgical system in accordance with the principles of the present disclosure.
Figure 10:
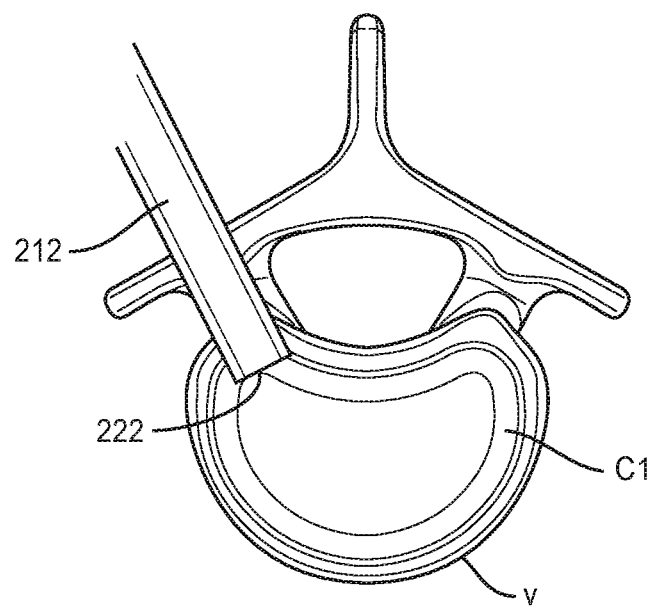
FIG. 10 is an axial view of components of one embodiment of a surgical system in accordance with the principles of the present disclosure disposed with vertebrae.
Figure 11:
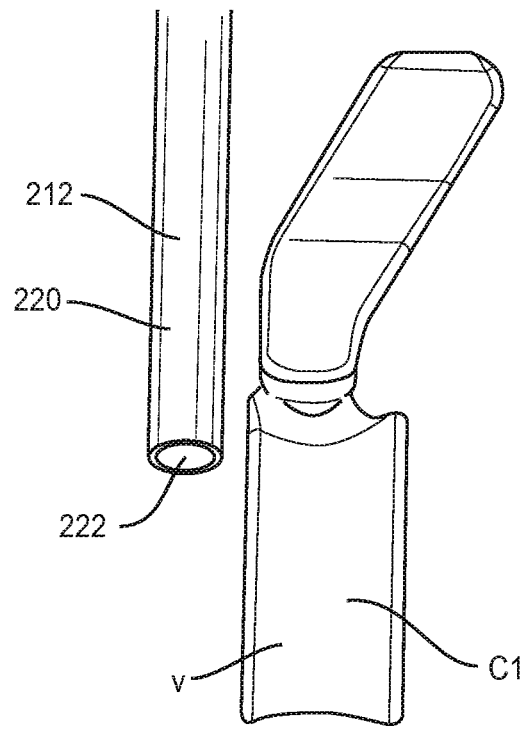
FIG. 11 is a lateral view of the components and vertebrae shown in FIG. 10.

Surgical system 10, similar to the systems and methods described herein, is employed in connection with one or more surgical procedures for tracking movement of surgical instrument 12, and acquiring and/or capturing data points, images and/or snap shots of tip 24 at one or a plurality of time intervals with projection 26 extending therefrom in connection with display of path P from computer monitor 66 to calculate the volume of intervertebral disc space C. During a surgery, surgical instrument 12 is configured for disposal adjacent a surgical site such that navigation component 58 is oriented relative to a sensor array 60, as shown in FIG. 9, to facilitate communication between navigation component 58 and sensor array 60. Distal end 22 of surgical instrument 12 is inserted into intervertebral disc space C.

Navigation system 14 executes one or more instructions and/or programming for tracking movement of surgical instrument 12 and acquiring data points that represent a position and/or orientation of surgical instrument 12 for generating data points, images and/or snap shots of tip 24 at one or a plurality of time intervals for generating projections 26 in connection with display of path P from computer monitor 66 to calculate the volume of tissue cavity C, as shown in FIGS. 5-7. Surgical instrument 12, with emitter array 62 attached thereto as described herein, is selectively disposed with intervertebral disc space C. Surgical instrument 12 can be manipulated relative to intervertebral disc space C. Orientation of navigation component 58 relative to sensor array 60 facilitates communication between navigation component 58 and sensor array 60 during the surgical procedure, as described herein. Sensor array 60 receives signals from emitter array 62 to provide information including the data points, as described herein, regarding the configuration, spatial position and/or trajectory of projection 26 relative to intervertebral disc space C. In some embodiments, surgical navigation system 14 provides for real-time tracking of surgical instrument 12.

Emitter array 62 generates a signal including the data points that represent a three-dimensional position of surgical instrument 12 relative to intervertebral disc space C to generate imaging of distal end 22 from an axial view of vertebrae and/or a lateral view of vertebrae. Emitter array 62 communicates the signal including the data points to the processor of computer 65. The processor measures, calibrates, samples, captures and/or identifies the size, configuration and/or three-dimensional position of distal end 22 in a three-dimensional space and generates an image of the data points of distal end 22 for display from monitor 66, as described herein. See, for example, the surgical systems and methods described in U.S. Pat. No. 8,571,638, the contents of which being hereby incorporated by reference herein in its entirety. The processor of computer 65 is programed with selected parameters, for example, volume V1 of projection 26.

Navigation system 14 executes instructions and/or programming to track movement of surgical instrument 12 and generate data points, images and/or snap shots of tip 24 at time intervals of 0.5 seconds and projects projections 26 having a selected volume of 1.5 cc, for example, projections 26, 26a, 26b, 26c, 26d, 26e, which are displayed from computer monitor 66 at positions P1, P2, P3, P4, P5 and P6, as shown in FIG. 5. Surgical navigation system 14 executes instructions to selectively stop data point capture with tip 24, for example, upon indication, highlight and/or measurement of a selected area of intervertebral disc space C.

Navigation system 14 executes instructions and/or programming to calculate a total volume V2 of path P corresponding to the selected area and height of intervertebral disc space C based on the selected volume of projections 26, as described herein. The present algorithm calculates a volume V2 of the selected area of intervertebral disc space C from projections 26, 26a, 26b, 26c, 26d and 26e, each having the selected volume V1, in connection with determining an implant size and configuration and/or an amount of bone growth promoting material in connection with surgical planning and performing surgical procedures, as shown in FIG. 7.

$$V2 = 6 \times (1.5 \text{ cc}) = 8.0 \text{ cc}$$

The images of projections 26, 26a, 26b, 26c, 26d and 26e overlap such that navigation system 14 executes instructions and/or programming to identify and/or determine the overlap of projections 26, for example, overlap O1 (0.25 cc), overlap O2 (0.25 cc), overlap O3 (0.3 cc), overlap O4 (0.3 cc) and overlap O5 (0.25 cc), as shown in FIG. 7. The present algorithm calculates actual volume VG of the selected area of intervertebral disc space C by subtracting overlap O1, overlap O2, overlap O3, overlap O4 and overlap O5 from volume V2 to calculate volume VG. The present algorithm calculates volume VG of tissue cavity C, in connection with determining an implant size and configuration and/or an amount of bone growth promoting material in connection with surgical planning and performing surgical procedures, as shown in FIG. 8.

$$VG = V2 - (O1 + O2 + O3 + O4 + O5)$$
$$= (8.0 \text{ cc}) - ((0.2 \text{ cc}) + (0.2 \text{ cc}) + (0.25 \text{ cc}) +$$
$$(0.25 \text{ cc}) + (0.2 \text{ cc}))$$
$$VG = 6.9 \text{ cc}$$

Surgical system 10 employs surgical instrument 12 and surgical navigation system 14, as described herein, with a method of assessing a graft volume of 6.9 cc of bone graft material for injection via the funnel configuration of distal end 22 with the selected area of intervertebral disc space C, as described herein, in connection with surgical planning and performing one or more surgical procedures. As such, surgical navigation system 14 is employed with a method for calculating an approximate graft volume, for example, 6.9 cc of bone graft material for injection with intervertebral disc space C. In some embodiments, surgical instrument 12 and surgical navigation system 14, as described herein, are employed with a method for determining an amount of intervertebral disc and/or vertebrae preparation, for example, the amount of intervertebral disc area and/or vertebrae that needs to be removed in connection with surgical planning and performing surgical procedures. In some embodiments, surgical instrument 12 and surgical navigation system 14, as described herein, are employed with a method for determining an amount of graft needed to be harvested from a patient and/or from non-patient sources and/or synthetics. Upon completion of one or more surgical procedures, the surgical instruments and non-implanted components of surgical system 10 are removed and the incision(s) are closed.

In one embodiment, surgical system 10, similar to the systems and methods described herein, includes a surgical instrument, for example, a trial instrument 212, as shown in FIGS. 10-25. Trial instrument 212 is employed with surgical navigation system 14, as described herein, and utilized for an intra-operative assessment of a volume of a tissue cavity C1, for example, an intervertebral disc space, for determining an implant size and configuration and/or an amount of bone growth promoting material, for example, bone graft for disposal with tissue cavity C1 in connection with surgical planning and performing surgical procedures, as described herein.

Trial instrument 212 includes a shaft 220 having a distal end 222 configured for disposal adjacent tissue cavity C1. Trial instrument 212 includes navigation component 58, as described herein, which communicates with surgical navigation system 14 to monitor components of surgical system 10 and patient anatomy under surgical navigation. Shaft 220 is positioned a selected distance from vertebral tissue in connection with surgical navigation and for generating an image of distal end 222 for display from computer monitor 66, as described herein.

Distal end 222 extends a distance measured from a proximal most end surface of shaft 220 in connection with image guidance. In some embodiments, this configuration provides indicia of the size, type and/or position of distal end 222 relative to shaft 220 and/or vertebral tissue. Surgical instrument 212 includes an image guide, for example, navigation component 58, as described herein, which communicates with surgical navigation system 14 to monitor components of surgical system 10 and patient anatomy under surgical navigation. Shaft 220 is positioned a selected distance from vertebral tissue in connection with surgical navigation and for generating an image of distal end 222 for display from computer monitor 66, as described herein. The components of surgical system 10 and surgical navigation system 14 allow a surgeon to determine a size and/or configuration of tissue cavity C1 for disposal of a selected volume of bone graft by projecting an image of a selected configuration from distal end 222 from a computer display.

Figure 12:
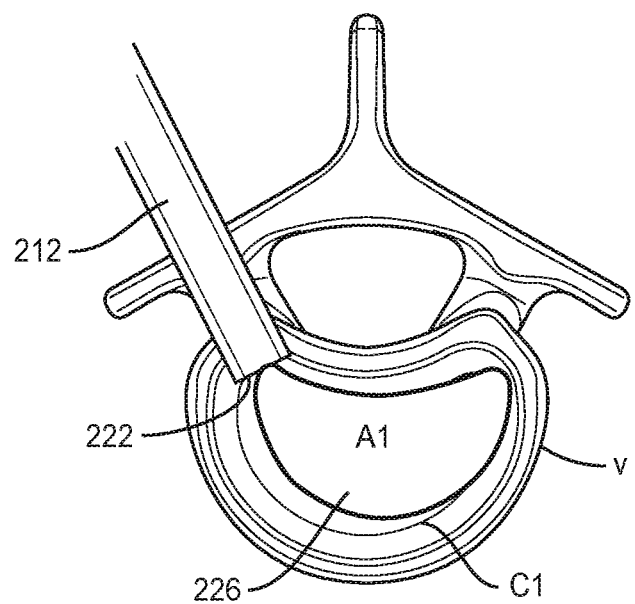
FIG. 12 is a graphical representation of a computer display of components of one embodiment of a surgical system in accordance with the principles of the present disclosure disposed with an axial view of patient anatomy.
Figure 13:
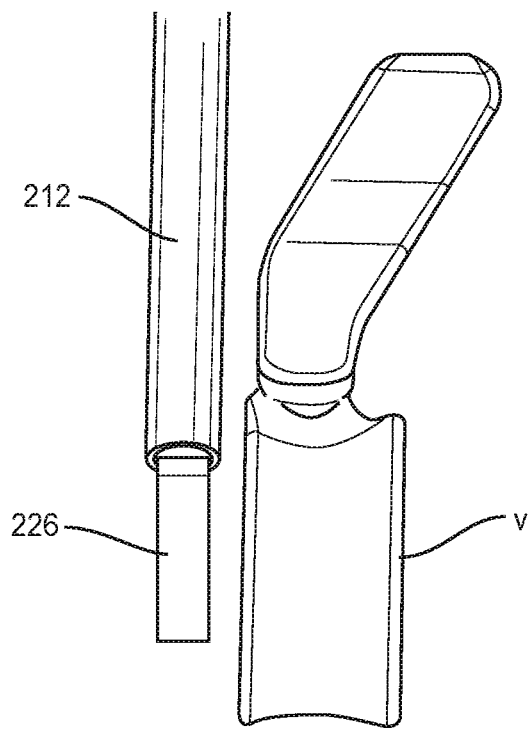
FIG. 13 is a lateral view of the components and patient anatomy shown in FIG. 12.

In some embodiments, three-dimensional scans of selected patient vertebral tissue are captured, via image capture and/or medical imaging as described herein, prior to the surgical procedure. In some embodiments, projection 226 is displayed on a previously captured image of patient vertebrae. Surgical navigation system 14 is configured to project an image of a selected configuration, for example, a trial projection 226 from distal end 222, as shown in FIG. 12. In some embodiments, the selected configuration may have alternate configurations, for example, kidney bean shaped, oval, circular, rectangular, triangular, oblong, barrel shaped, dog bone shaped, t shaped, undulating, staggered and/or offset.

Projection 226 is displayed from end 222. Projection 226 includes a selected volume, a selected surface area and/or the selected configuration of projection 226 includes selected measurements or indicia in two or three dimensions, for example, length, width, and height to calculate the volume of tissue cavity C1 for determining an implant size and configuration and/or an amount of bone growth promoting material in connection with surgical planning and performing surgical procedures. In some embodiments, projection 226 is selected from a plurality of alternately sized projections 226. In some embodiments, the selected configuration includes a volume selected from a range of greater than zero through 12.0 cc.

In some embodiments, projection 226 is shown relative to a saved image of the intervertebral cavity. The surgeon can view trial instrument 212 and tissue cavity C1 at various orientations, for example, axial and/or lateral, as described herein. In some embodiments, one or more processors and/or software of surgical navigation system 14 executes one or more instructions and/or programming for tracking movement of trial instrument 212, and generating data points, images and/or snap shots of distal end 222 with projection 226 displayed from computer monitor 66 for alignment with tissue cavity C1 and/or to calculate the volume of tissue cavity C1. In some embodiments, one or more processors and/or software of surgical navigation system 14 execute one or more instructions and/or programming in operation of image capturing portion 70, described herein, for acquiring and/or capturing data points, images and/or snap shots of distal end 222 with projection 226 for alignment with tissue cavity C1 and/or to calculate the volume of tissue cavity C1.

Figure 14:
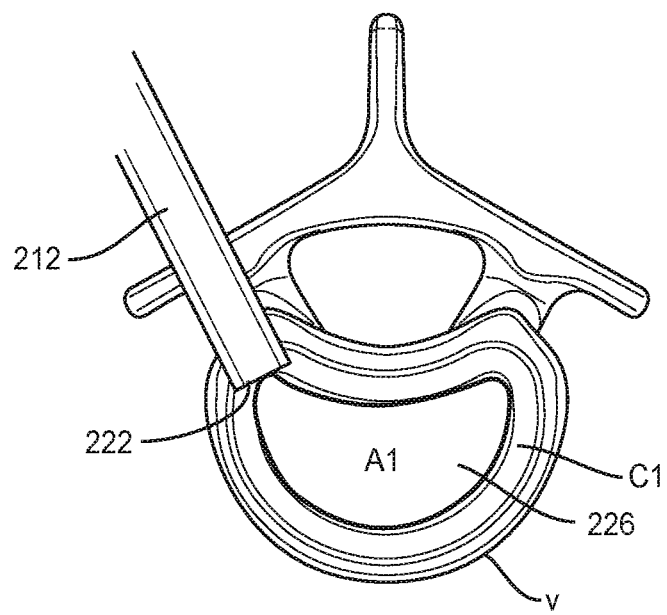
FIG. 14 is a graphical representation of a computer display of components of one embodiment of a surgical system in accordance with the principles of the present disclosure disposed with an axial view of patient anatomy.

In some embodiments, projection 226 has, for example, a surface area A1, which may be projected initially to compare area A1 of projection 226 relative to tissue cavity C1, as shown in FIG. 12. Surgical navigation system 14 tracks movement of trial instrument 212 and generates data points of projection 226 for imaging of projection 226 for display from computer monitor 66. Projection 226 is manipulated for alignment with tissue cavity C1 to compare and/or assess area A1 relative to tissue cavity C1 to determine that area A1 sufficiently occupies tissue cavity C1, as shown in FIG. 14. In some embodiments, projection 226 having area A1 includes a fixed or a variable height, as described herein, to calculate the volume of tissue cavity C1.

Figure 15:
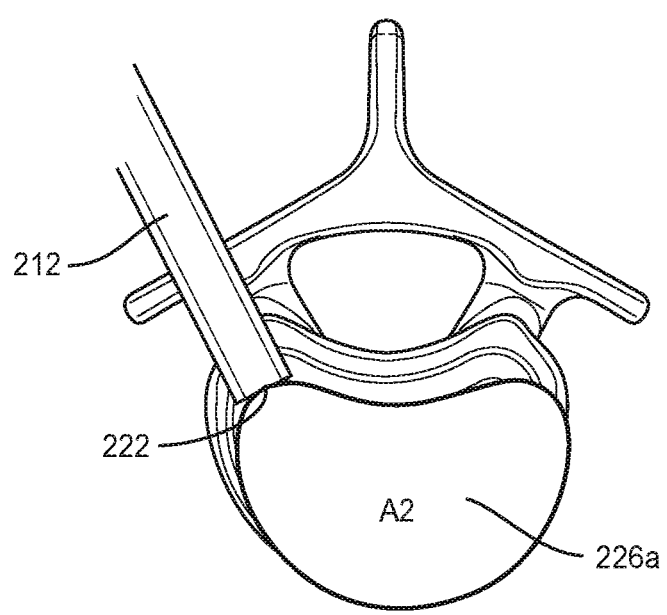
FIG. 15 is a graphical representation of a computer display of components of one embodiment of a surgical system in accordance with the principles of the present disclosure disposed with an axial view of patient anatomy.
Figure 16:
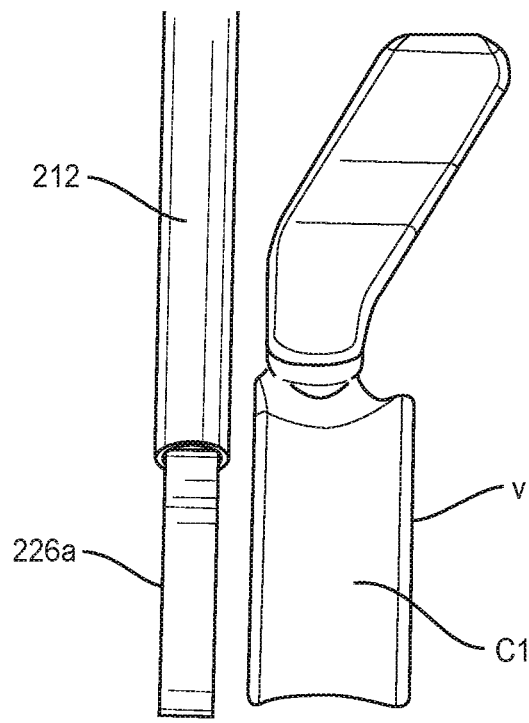
FIG. 16 is a lateral view of the components and patient anatomy shown in FIG. 15.
Figure 17:
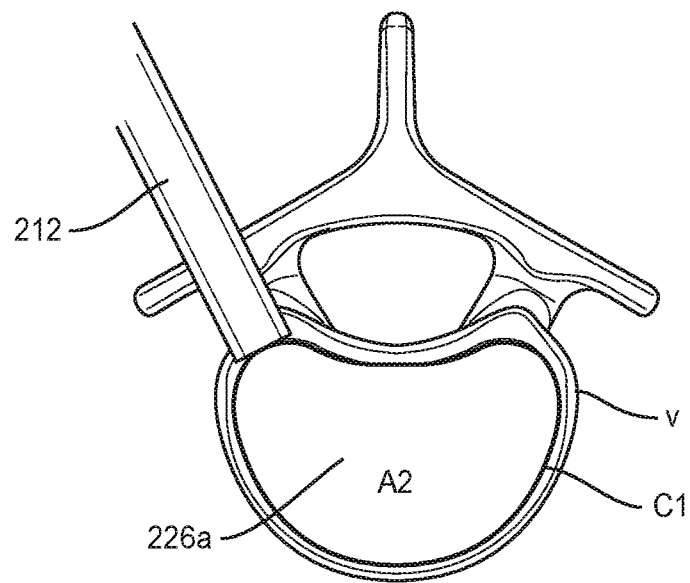
FIG. 17 is a graphical representation of a computer display of components of one embodiment of a surgical system in accordance with the principles of the present disclosure disposed with an axial view of patient anatomy.

In some embodiments, a different, for example, larger projection 226 may be viewed for assessment and/or comparison such that a second projection 226a having, for example, a surface area A2 is projected, as shown in FIGS. 15 and 16. Surgical navigation system 14 tracks movement of trial instrument 212 and generates data points of projection 226 for imaging of projection 226a for display from computer monitor 66. Projection 226a is manipulated for alignment with tissue cavity C1 to compare and/or assess surface area A2 relative to tissue cavity C1 to determine that surface area A2 sufficiently occupies tissue cavity C1, as shown in FIG. 17. In some embodiments, projection 226 having area A2 includes a fixed or a variable height, as described herein, to calculate the volume of tissue cavity C1.

Figure 18:
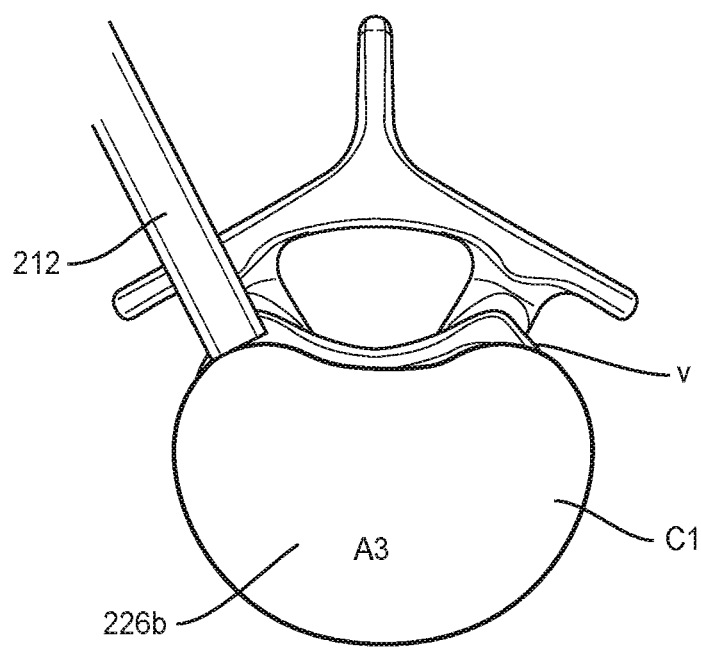
FIG. 18 is a graphical representation of a computer display of components of one embodiment of a surgical system in accordance with the principles of the present disclosure disposed with an axial view of patient anatomy.
Figure 19:
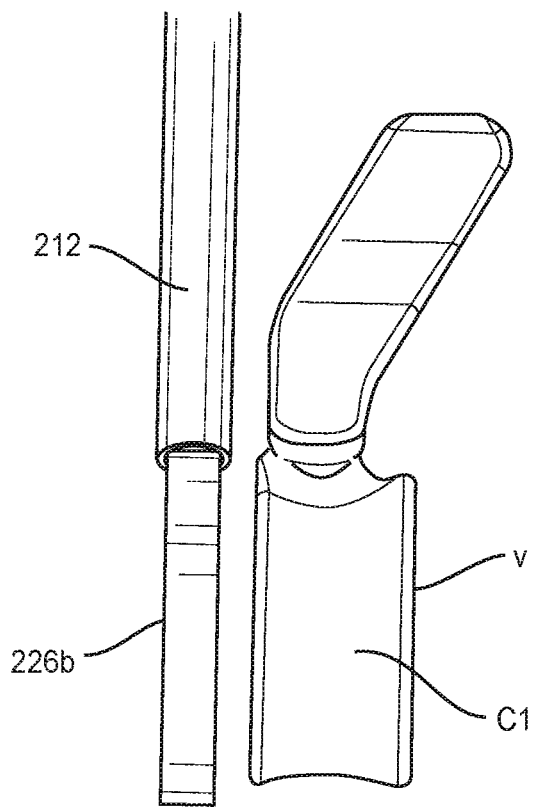
FIG. 19 is a lateral view of the components and patient anatomy shown in FIG. 18.
Figure 20:
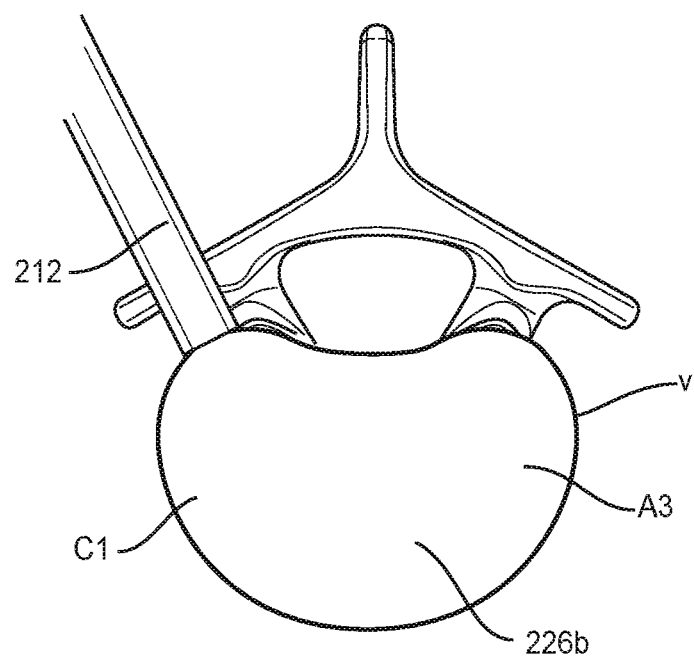
FIG. 20 is a graphical representation of a computer display of components of one embodiment of a surgical system in accordance with the principles of the present disclosure disposed with an axial view of patient anatomy.
Figure 21:
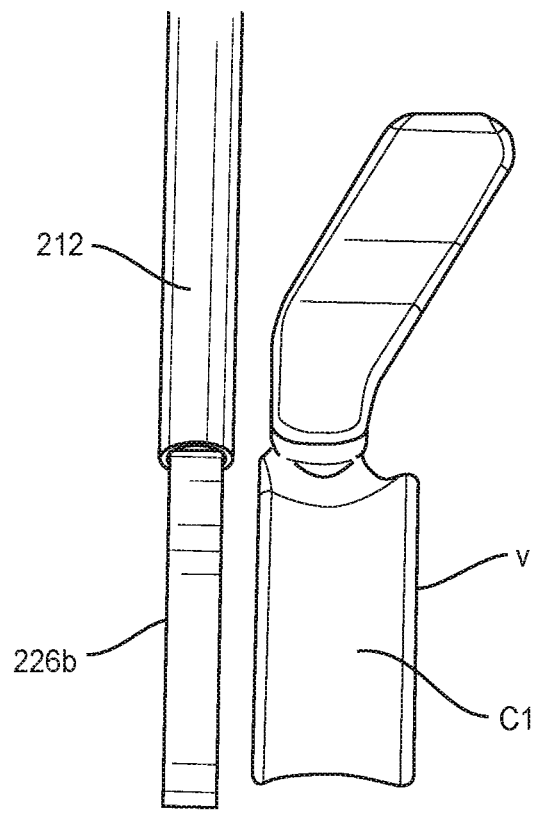
FIG. 21 is a lateral view of the components and patient anatomy shown in FIG. 20.
Figure 22:
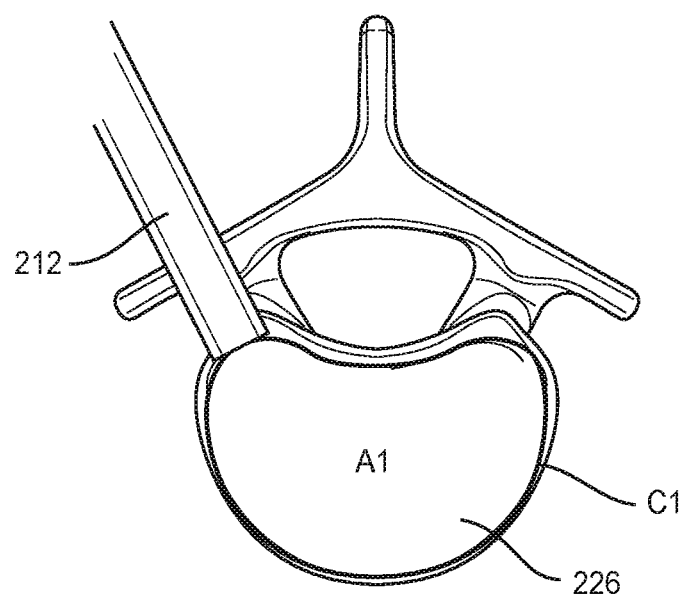
FIG. 22 is a graphical representation of a computer display of components of one embodiment of a surgical system in accordance with the principles of the present disclosure disposed with an axial view of patient anatomy.
Figure 23:
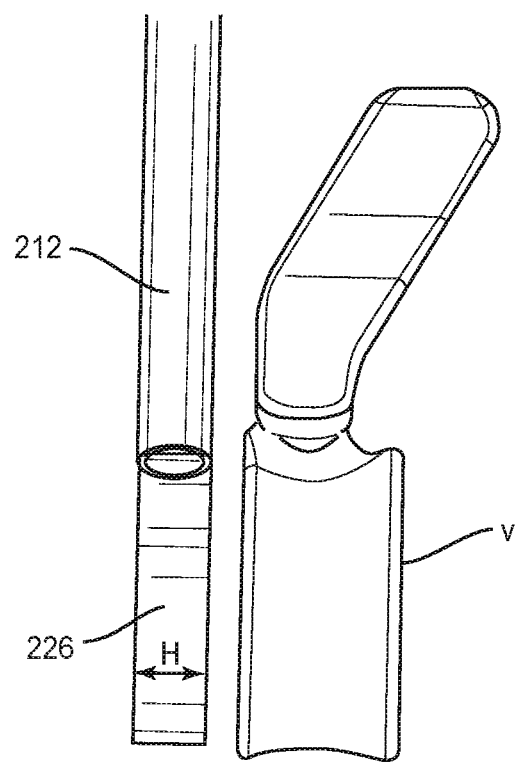
FIG. 23 is a lateral view of the components and patient anatomy shown in FIG. 22.
Figure 24:
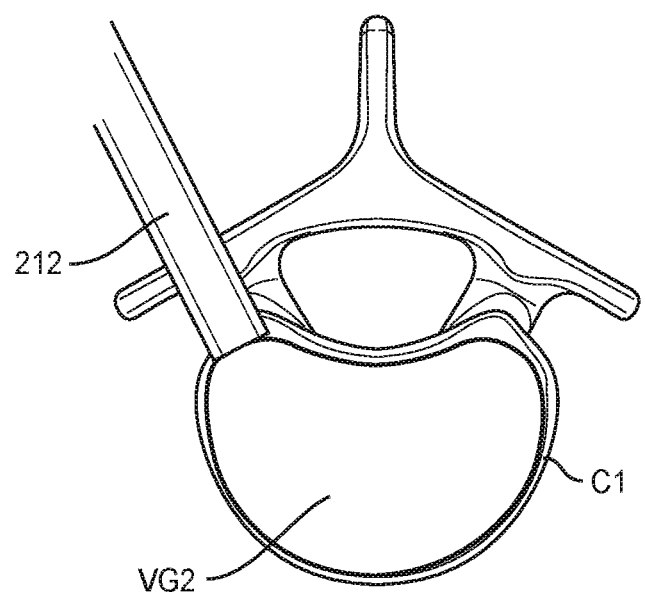
FIG. 24 is a graphical representation of a computer display of components of one embodiment of a surgical system in accordance with the principles of the present disclosure disposed with an axial view of patient anatomy.
Figure 25:
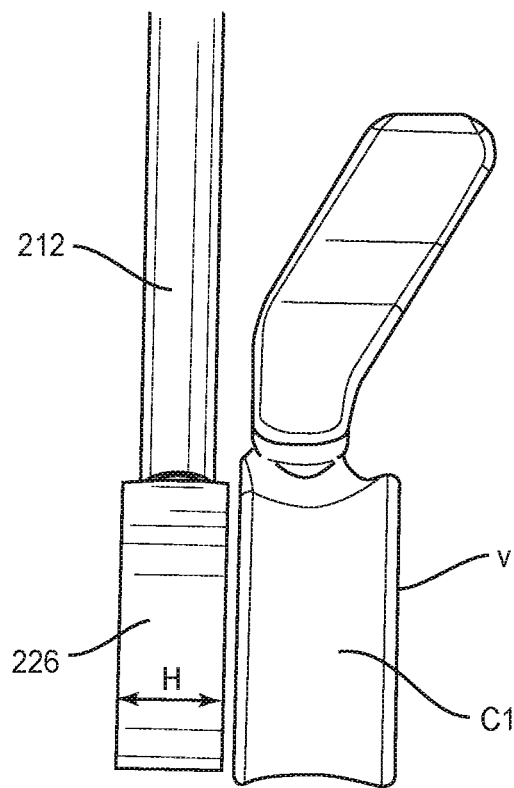
FIG. 25 is a lateral view of the components and patient anatomy shown in FIG. 24.

In some embodiments, a different, for example, larger projection 226 may be viewed for assessment and/or comparison such that a third projection 226b having, for example, a surface area A3 is projected, as shown in FIGS. 18 and 19. Surgical navigation system 14 tracks movement of trial instrument 212 and generates data points of projection 226 for imaging of projection 226b for display from computer monitor 66. Projection 226b is manipulated for alignment with tissue cavity C1 to compare and/or assess area A3 relative to tissue cavity C1 to determine that area A3 sufficiently occupies tissue cavity C1, as shown in FIGS. 20 and 21. In some embodiments, projection 226 having area A3 includes a fixed or a variable height, as described herein, to calculate the volume of tissue cavity C1.

In some embodiments, third projection 226b is greater than a size of tissue cavity C1 as it would require removal of tissue that may compromise the annulus and/or injure the patient. As such, a surgeon may select a surface area of projection 226. In some embodiments, utilizing projections rather than physical trial instruments resists and/or prevents damage or injury to the intervertebral space.

In some embodiments, projection 226 is manipulated to adjust a height H of projection 226 to determine and/or calculate, and compare to a height of tissue cavity C1, as shown in FIGS. 22-25. Surgical navigation system 14 tracks movement of trial instrument 212 and generates data points of projection 226, as described herein, corresponding to height H of projection 226 for generating imaging of height H of projection 226 for display from computer monitor 66. Adjusting height H is utilized to determine if the volume of the selected projection 226 sufficiently occupies tissue cavity C1 and determines a volume VG2 of bone graft needed to fill tissue cavity C1. In some embodiments, an algorithm calculates volume VG2 of tissue cavity C1 from projection 226 having an initial surface area and/or height, in connection with determining an implant size and configuration and/or an amount of bone growth promoting material in connection with surgical planning and performing surgical procedures. For example, area A=13.7 cm$^2$ and height H=10 mm. In some embodiments, the value of VG2 is displayed on or near projection 226 so that the calculated volume is easily visible.

$$VG2 = A \times H$$
$$= (13.7 \text{ cm}^2) \times (10 \text{ mm})$$
$$VG2 = 13.7 \text{ cc}$$

Surgical system 10 employs surgical instrument 212 and surgical navigation system 14, as described herein, with a method of assessing a graft volume of bone graft material for injection via a funnel configuration of distal end 222 with the selected area of intervertebral disc space C1, as described herein, in connection with surgical planning and performing one or more surgical procedures. As such, surgical navigation system 14 is employed with a method for calculating an approximate graft volume of bone graft material for injection with intervertebral disc space C1. In some embodiments, surgical instrument 212 and surgical navigation system 14, as described herein, are employed with a method for determining an amount of intervertebral disc and/or vertebrae preparation, for example, the amount of intervertebral disc area and/or vertebrae that needs to be removed in connection with surgical planning and performing surgical procedures. In some embodiments, surgical instrument 212 and surgical navigation system 14, as described herein, are employed with a method for determining an amount of graft needed to be harvested from a patient and/or from non-patient sources and/or synthetics.

In some embodiments, projection 226 may include indicia indicating a size of projection, for example, small, medium, large and height. In some embodiments, a selected configuration of projection 226 may conform in size with a vertebral endplate or a partial vertebral endplate, for example, for partial corpectomies. In some embodiments, projection 226 may include indicia indicating an approximate vertebral endplate size, for example, height, length and/or width. In some embodiments, surgical system 10 may be utilized for assessing various anatomical graft volumes, for example, tibial holes, corpectomies, oral, maxillofacial gaps, graft volumes of posterior lateral spaces and/or assessing other anatomic features, foraminal height and/or canal foramen. Upon completion of one or more surgical procedures, the surgical instruments and non-implanted components of surgical system 10 are removed and the incision(s) are closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for treating a spine, the method comprising:
   positioning a distal end of a cannulated shaft of a surgical instrument into an intervertebral cavity, the surgical instrument including a tracking device oriented relative to a sensor to communicate a signal representative of a position of the distal end of the cannulated shaft of the surgical instrument relative to the intervertebral cavity;

operating a display to display an image of the intervertebral cavity:

operating a navigation system to track at a first time the distal end of the cannulated shaft at a first position within the intervertebral cavity:

operating the navigation system to track at a second time the distal end of the cannulated shaft at a second position within the intervertebral cavity;

operating a processor to:

project overlapping images of spheres on the displayed image of the intervertebral cavity based on at least the first position and the second position;

determine a volume of the intervertebral cavity based on the data projected overlapping images of spheres; and delivering bone graft through the cannulated shaft and into the intervertebral cavity.

2. A method for treating a spine, the method comprising:

providing a shaft of a surgical instrument configured to be positioned adjacent to a tissue cavity;

providing the shaft for delivery of bone graft through the shaft and into the tissue cavity;

providing a tracking device with the surgical instrument to communicate a signal representative of a position of distal end of the shaft of the surgical instrument relative to the tissue cavity;

operating a processor to:

display an image of the tissue cavity, track the distal end of the shaft relative to the tissue cavity, project overlapping projections from the distal end of the shaft of the shaft at the tracked position of the distal end of the shaft on the displayed image of the tissue to generate data for display of the projected overlapped projections relative to the image of the tissue cavity; and comparing the projected overlapped projections relative to the image of the tissue cavity to determine a volume of the tissue cavity.

3. The method as recited in claim 2, wherein the projected overlapping projections each include a kidney bean shape.

4. The method as recited in claim 2, further comprising calculating a volume of bone graft for disposal within the tissue cavity based on the determined volume of the tissue cavity.

5. The method as recited in claim 2, wherein the projected overlapping projections each include a different size.

6. A method for evaluating a subject, comprising:

providing a surgical instrument having a shaft configured for insertion relative to a tissue cavity of the subject;

providing a tracking device associated with the surgical instrument;

providing the tracking device to communicate a signal representative of a position of at least a distal end of the shaft relative to the tissue cavity;

displaying an image of the tissue cavity;

displaying a projection extending out from the distal end of the shaft on the displayed image of the tissue cavity;

tracking movement the tracking device;

communicating with a processor the tracked movement of the tracking device to generate data for display of a movement of the projection; and determining a volume of the tissue cavity based on the communicated tracked movement of the tracking device that generated data for display of the movement of the projection.

7. The method as recited in claim 6, wherein the shaft terminates at the distal end.

8. The method as recited in claim 6, wherein the spheres are different in size from the distal end.

9. The method as recited in claim 8, wherein the spheres are different in shape from the distal end.

10. The method of claim 8, wherein determining the volume of the tissue cavity includes projecting overlapping images of spheres from the distal end of the shaft when the distal end is positioned relative to the tissue cavity.

11. The method of claim 6, wherein the provided instrument having the shaft has the shaft configured as a cannulated shaft, wherein the cannulated shaft is configured for delivery of bone graft through the cannulated shaft and into the tissue cavity of the subject.

12. The method of claim 6, further comprising:

providing the distal end as a funnel.

13. The method of claim 6, further comprising:

providing the distal end in an angled configuration.

14. The method of claim 6, wherein tracking movement of the tracking device includes movement in a plane of the tissue cavity.

15. The method of claim 6, wherein tracking movement of the tracking device includes movement in a first dimension, a second dimension and a third dimension of the tissue cavity.

16. The method of claim 6, wherein tracking movement of the tracking device includes acquiring data corresponding to the images.

17. The method of claim 6, wherein tracking movement of the tracking device includes acquiring data captured at discrete time intervals.

18. The method of claim 6, wherein determining the volume includes a calculation based on the images.

19. The method of claim 6, wherein determining the volume includes adding volumes of the images.

20. The method of claim 6, wherein determining the volume includes calculating a volume of bone graft for disposal within the tissue cavity based on the determined volume.

* * * * *

UNITED STATES PATENT AND TRADEMARK OFFICE
CERTIFICATE OF CORRECTION

PATENT NO. : 11,890,205 B2
APPLICATION NO. : 16/713952
DATED : February 6, 2024
INVENTOR(S) : Jonathan M. Dewey et al.

It is certified that error appears in the above-identified patent and that said Letters Patent is hereby corrected as shown below:

On the Title Page

Column 1, item (72) Inventors, Line 3, After "C", insert --.--

In the Claims

Column 19, Line 2, In Claim 1, delete "cavity:" and insert --cavity;-- therefor

Column 19, Line 5, In Claim 1, delete "cavity:" and insert --cavity;-- therefor

Column 19, Line 14, In Claim 1, after "the", delete "data"

Column 19, Line 24, In Claim 2, before "distal", insert --a--

Column 20, Lines 14-15, In Claim 8, delete "8. The method as recited in claim 6, wherein the spheres are different in size from the distal end." and insert --8. The method of claim 6, wherein determining the volume of the tissue cavity includes projecting overlapping images of spheres from the distal end of the shaft when the distal end is positioned relative to the tissue cavity.-- therefor Column 20, Lines 18-21, In Claim 10, delete "10. The method of claim 8, wherein determining the volume of the tissue cavity includes projecting overlapping images of spheres from the distal end of the shaft when the distal end is positioned relative to the tissue cavity." and insert --10. The method as recited in claim 8, wherein the spheres are different in size from the distal end.-- therefor Signed and Sealed this
Ninth Day of July, 2024

Katherine Kelly Vidal
*Director of the United States Patent and Trademark Office*